United States Patent [19]
Kemp et al.

[11] Patent Number: 5,126,264
[45] Date of Patent: Jun. 30, 1992

[54] THE RESA AND FIRA ANTIGENS OF PLASMODIUM FALCIPARUM

[75] Inventors: David J. Kemp, North Balwyn; Robin F. Anders, North Melbourne; Ross Coppel, Armadale; Graham V. Brown, Balwyn Victoria; Robert B. Saint, Lower Templestowe; Alan E. Cowman, North Carlton; Albert E. Bianco, Ascot Vale; Graham F. Mitchell, Lower Templestowe, all of Australia

[73] Assignee: The Walter & Eliza Hall Institute of Medical Research, Australia

[21] Appl. No.: 554,946

[22] Filed: Jul. 16, 1990

Related U.S. Application Data

[63] Continuation of Ser. No. 862,357, filed as PCT/AU85/00223, Sep. 10, 1985, abandoned.

[30] Foreign Application Priority Data

Sep. 11, 1984 [AU] Australia ............... PG7066/84
Sep. 11, 1984 [AU] Australia ............... PG7067/84

[51] Int. Cl.⁵ .............. C12N 1/20; C12N 15/00; C12P 21/06; C12P 19/34
[52] U.S. Cl. .............. 435/252.33; 435/69.1; 435/91; 435/172.3; 435/235.1; 536/27; 530/350; 935/18; 935/31; 935/47; 935/58; 935/65; 935/73; 935/81
[58] Field of Search ............ 435/69.1, 91, 172.3, 435/235, 252.33, 320; 536/27; 530/350; 935/18, 31, 47, 58, 65, 73, 81

[56] References Cited

U.S. PATENT DOCUMENTS 4,466,917 8/1984 Nussenzweig et al. ............ 260/112

FOREIGN PATENT DOCUMENTS

WO84/02917 8/1984 PCT Int'l Appl.
WO84/02922 8/1984 PCT Int'l Appl.
2091268 7/1982 United Kingdom.

OTHER PUBLICATIONS

Kemp, D. J. et al. Proc Nat'l Acad Sci-U.S.A. vol. 80 pp. 3787-3791 (1983).
Coppel, R. L. et al. Nature vol. 310 pp. 789-792 (1984).
Chemical Abstracts, 192681r, vol. 98, 1983, p. 170.
Proc. Natl. Acad. Sci. U.S.A. vol. 80, pp. 3787-3791, Jun. 1983, Immunology.
Chemical Abstracts, 67168g, vol. 97, 1982, p. 152.
Molecular and Biochemical Parisitology, 5 (1982), 391-400, Elsevier Biomedical Press, p. 391.
Nature, vol. 297, Jun. 17, 1982, pp. 591-593.
Antigenic Diversity in the Human Malaria Parasite *Plasmodium falciparum*, Science, vol. 217, Jul. 16, 1982, pp. 254-257.
Nature vol. 306, Dec. 1983, pp. 751-756.
Biochemical Abstracts, I. Cell Biochem. Suppl. 1983, vol. 0, No. 7, Part A, p. 3.
"Molecular Cloning", T. Maniattis, E. F. Fritsch, J. Sambrook, Cold Spring Harbor Laboratory 1982, pp. 17-18.
Phil. Trans. R. Soc. Lond. B. 307, 179-187 (1984) "The expression of *Plasmodium falciparum* bloodstage antigens in *Escherichia coli*".
Mol. Biol. Med. (1984) 2, 177-191, "*Plasmodium falciparum* complementary DNA Clones Expressed in *Escherichi coli* Encode many Distinct Antigens".

Primary Examiner—Richard A. Schwartz
Assistant Examiner—Joan Ellis
Attorney, Agent, or Firm—Sughrue, Mion, Zinn, Macpeak & Seas

[57] ABSTRACT

DNA molecules comprising polynucleotide sequences substantially corresponding to all or a portion of the base sequence coding for an antigen of *Plasmodium falciparum* selected from the group consisting of the RESA antigen, the FIRA antigen, and other antigens of *P. falciparum* cross-reactive therewith. Such DNA molecules are capable of being expressed as polypeptide(s). Synthetic peptides or polypeptides displaying the antigenicity of all or a portion of the RESA or FIRA antigens of *P. falciparum*. Compositions for stimulating immune responses against *P. falciparum* antigens in a mammal, comprising at least one polypeptide displaying the antigenicity of the RESA or FIRA antigens of *P. falciparum*.

11 Claims, 23 Drawing Sheets

```
AT TCCAATCCCTTTTTTTTTTTTTCTTTTCTTTTTTTACTTATT
   10        20        30        40

TAATSCAATAAAATAAAAATAAAATAAATAAATAAATTTATTTAAT
   100       110       120       130

TGGTTAAATTTTAAAATATATAAAATACTTTACTGTGGTTGAATTA
   190       200       210       220

TGGTTGTTATATATTTGTTCTTTTTTATTTTGATAAAATACAAAAA
   280       290       300       310

TAATTTTTTTTTATTTTTTTATATTTATGTATTTTTGTTAGAAA
   370       380       390       400

AATATTTTTTTTTATTATTTATATGATAGCGAAAAAAAAAAAAA
   460       470       480       490

TATTTATATATTATTTTTTTTTTTTTTTATATATTTTATATAAA
   550       560       570       580

ATTTATAATAATATTTTTTTTTTCTAGAAAAAAAAAATTTACTATT
   640       650       660       670

AAAAAAAAAAAAAAAAAAAAATTACTTGGTTTTAATTTTTTACTTTT
   730       740       750       760

HisAlaTyrSerTrpIlePheSerGlnGlnTyrMetGlyThrLy
         TTCATGCATATAGTTGGATTTTTTCTCAACAATATATGGGTACAAA
            820       830       840       850

GluLysArgAsnGluAsnLysSerPheLeuLysValLeuCysSe
         AAGAAAAAAGAAATGAAAATAAGAGCTTTTTAAAGGTGTTGTGTTC
            910       920       930       940

Asn
TAAATGTAAGTTTTTTTTTTTTTTTTTTTTTTTGAAATAAAATACA
   1000      1010      1020      1030

ATTCTATTCTTTTTTATATGTCATGCATATTTTATATATTATAATA
   1090      1100      1110      1120

GlyAsnLeuGlyTyrAsn
TTTTTTTTTTTTTTTTTTTTTTTTCATAGGGTAATCTTGGATATAAT
   1180      1190      1200      1210

AsnLeuTyrGlyGluThrLeuProValAsnProTyrAlaAspSer
AAATTTATACGGGGAAACATTGCCAGTAAACCCATATGCTGATTCT
   1270      1280      1290      1300
```

*FIG. 1(A)a.*

```
ATATTTTTTATTAAGTGAAAAAAAAAAAAAAAAAAAAATAATAA
    50        60        70        80        90

AATTTTTATATAGATTTAATATATATCGGTTGATAGATTTCGTT
    140       150       160       170       180

TTAAAAAAAAAAAATAATAAATAAATTAAAAGCTTCCTTATTCT
    230       240       250       260       270

AAAAATAATAAAACCTAATTATAAAAAAAAAATAAAAGTTCATA
    320       330       340       350       360

AAAAAAAAAAAAAAAAAAAAGAAATAATTTATTTATAATATATA
    410       420       430       440       450

AAAAAAATAAAATAATTTTTAAAAATATTTTATTATTATTAAAA
    500       510       520       530       540

TAACATTTTCTATAAATTAAATATATTTTAATATATATATATAT
    590       600       610       620       630

TTTATATTTATATATATTATAATATTATTTAGACATATTATTAA
    680       690       700       710       720

MetArgProPhe
ACATAATTTATAATAAGAAAATATCTAAATAATTATGAGACCTT
    770       780       790       800       810 sAsnValLysGluLysAsnProThrIleTyrSerPheAspAspGlu
AAATGTTAAGGAAAAAAATCCCACCATATATTCATTTGATGATG
    860       870       880       890       900 rLysArgGlyValLeuProIleIleGlyIleLeuTyrIleIleLeu
TAAACGTGGTGTTCTTCCAATTATTGGAATACTATATATCATTT
    950       960       970       980       990

TATTTTTTATATTTAATTTTTTATGTTAATGCTTATTTTATTTT
   1040      1050      1060      1070      1080

CCGTTTTTAATAATATATAATATATCTTTGTTATTATATATAAT
   1130      1140      1150      1160      1170

GlySerSerSerSerGlyValGlnPheThrAspArgCysSerArg
GGAAGTTCATCTTCTGGCGTACAATTTACTGATAGATGTTCAAG
   1220      1230      1240      1250      1260

GluAsnProIleValValSerGlnValPheGlyLeuProPheGlu
GAAAACCCAATAGTTGTAAGTCAGGTATTTGGTTTACCCTTCGA
   1310      1320      1330      1340      1350
```

*FIG. 1(A)b*

```
LysProThrPheThrLeuGluSerProProAspIleAspHisThr
AAAACCTACGTTTACCTTAGAAAGTCCTCCTGATATTGATCATACA
     1360      1370      1380      1390

TyrArgTyrSerAsnAsnTyrGluAlaIleProHisIleSerGlu
ATATCGATATTCTAATAACTATGAAGCCATTCCTCATATAAGTGAG
     1450      1460      1470      1480

LysValAspAsnLeuGlyArgSerGlyGlyAspIleIleLysLys
AAAGGTTGATAACTTAGGAAGAAGTGGAGGAGACATTATAAAAAA
     1540      1550      1560      1570

TyrAspSerLeuLysGluLysLeuGlnLysThrTyrSerGlnTyr
ATATGATTCTTTAAAAGAAAAATTACAGAAAACTTACAGTCAGTAC
     1630      1640      1650      1660

ThrGlnCysIleLysLeuIleAspGlnGlyGlyGluAsnLeuGlu
GACACAATGCATAAAACTTATTGATCAAGGAGGAGAGAACCTTGAA
     1720      1730      1740      1750

LeuAsnLeuGluGluTyrArgArgLeuThrValLeuAsnGlnIle
TTTAAATCTTGAAGAATATAGAAGATTGACTGTGTTGAACCAAATC
     1810      1820      1830      1840

IleMetAsnSerAspIleSerSerPheLysHisIleAsnGluLeu
AATTATGAATAGTGACATTTCTTCCTTTAAACATATAAATGAATTG
     1900      1910      1920      1930

LysLysArgAlaGlnLysProLysLysLysLysSerArgArgGly
GAAGAAAAGAGCTCAAAAACCGAAGAAGAAAAAAAGTAGAAGAGGA
     1990      2000      2010      2020

GlnGluGluProValGlnThrValGlnGluGlnGlnValAsnGlu
ACAAGAAGAACCAGTCCAAACCGTTCAAGAACAACAAGTAAATGAA
     2080      2090      2100      2110

AlaIleAsnTyrTyrAspThrValLysAspGlyValThrLeuAsp
AGCTATTAATTATTATGATACCGTAAAAGATGGTGTATACTTAGAC
     2170      2180      2190      2200

AspLeuGluLysGlnLysTyrMetAspMetLeuAspThrSerGlu
TGATTTGGAAAAACAAAAATATATGGATATGTTAGATACATCTGAA
     2260      2270      2280      2290

GluHisValGluGluHisThrAlaAspAspGluHisValGluGlu
TGAACATGTAGAAGAACACACTGCTGATGACGAACATGTAGAAGAA
     2350      2360      2370      2380

AspGluHisValGluGluProThrValAlaGluGluHisValGlu
TGATGAACACGTAGAAGAACCAACTGTTGCTGAAGAACATGTAGAA
     2440      2450      2460      2470
```

*FIG. 1(B)a.*

```
AsnIleLeuGlyPheAsnGluLysPheMetThrAspValAsnArg
AATATTTTGGGTTTTAATGAGAAGTTCATGACTGATGTAAATAG
1400      1410      1420      1430      1440

PheAsnProLeuIleValAspLysValLeuPheAspTyrAsnGlu
TTCAATCCACTTATTGTAGATAAAGTTCTTTTCGACTATAACGA
1490      1500      1510      1520      1530

MetGlnThrLeuTrpAspGluIleMetAspIleAsnLysArgLys
ATGCAAACTTTATGGGATGAAATAATGGATATTAATAAAAGAAA
1580      1590      1600      1610      1620

LysValGlnTyrAspMetProLysGluAlaTyrGluSerLysTrp
AAGGTTCAATATGATATGCCAAAAGAAGCATATGAGAGCAAATG
1670      1680      1690      1700      1710

GluArgLeuAsnSerGlnPheLysAsnTrpTyrArgGlnLysTyr
GAAAGATTGAACTCACAATTTAAAAACTGGTACAGGCAGAAATA
1760      1770      1780      1790      1800

AlaTrpLysAlaLeuSerAsnGlnIleGlnTyrSerCysArgLys
GCTTGGAAAGCTTTATCCAACCAAATTCAATATTCATGCAGAAA
1850      1860      1870      1880      1890

LysSerLeuGluHisArgAlaAlaLysAlaAlaGluAlaGluMet
AAAAGTTTAGAACACAGAGCCGCAAAAGCTGCAGAAGCAGAAAT
1940      1950      1960      1970      1980

TrpLeuCysCysGlyGlyGlyAspIleGluThrValGluProGln
TGGTTATGTTGTGGGGGGGGAGATATCGAAACAGTTGAACCACA
2030      2040      2050      2060      2070

TyrGlyAspIleLeuProSerLeuArgAlaSerIleThrAsnSer
TATGGTGATATATTACCATCATTAAGGGCCAGTATTACTAATTC
2120      2130      2140      2150      2160

HisGluThrSerAspAlaLeuTyrThrAspGluAspLeuLeuPhe
CATGAAACATCAGATGCTCTTTATACAGATGAAGATTTGTTATT
2210      2220      2230      2240      2250

GluGluSerValGluGluAsnGluGluHisThrValAspAsp
GAAGAATCTGTTGAAGAAAATGAAGAAGAACACACTGTTGATGA
2300      2310      2320      2330      2340

ProThrValAlaAspAspGluHisValGluGluProThrValAla
CCAACTGTTGCTGATGATGAACATGTAGAAGAACCAACTGTTGC
2390      2400      2410      2420      2430

GluProThrValAlaGluGluHisValGluGluProAlaSerAsp
GAACCAACTGTTGCTGAAGAACACGTAGAAGAACCAGCTAGTGA
2480      2490      2500      2510      2520
```

*FIG. I(B).b.*

```
ValGlnGlnThrSerGluAlaAlaProThrIleGluIleProAsp
TGTTCAACAAACTTCAGAAGCAGCTCCAACAATTGAAATCCCCGAT
     2530      2540      2550      2560

AsnGluIleThrGluArgTyrPheLysLeuAlaGluAsnTyrTyr
GAACGAAATTACTGAACGTTATTTAAGTTAGCTGAAAATTACTAT
     2620      2630      2640      2650

ValAsnGluAlaTyrGlnValLeuGlyAspIleAspLysLysArg
AGTCAACGAAGCCTACCAAGTTTAGGAGATATTGATAAAAAAGA
     2710      2720      2730      2740

MetAsnProSerIlePheTyrLeuLeuSerSerLeuGluLysPhe
TATGAATCCATCCATCTTTTATTTATTATCTAGTTTAGAAAAATTT
     2800      2810      2820      2830

PhePheGluLysArgLeuSerMetAsnAspLeuGluAsnLysSer
CTTTTTTGAAAAGAGATTATCTATGAATGATTTAGAGAATAAAAGT
     2890      2900      2910      2920

AlaHisValSerGluTyrLeuLeuAsnIleLeuGlnProCysIle
AGCACATGTATCTGAATATTTATTAAATATATTACAACCATGTATA
     2980      2990      3000      3010

GlyLeuLysGlySerArgPheAspIleProIleLeuGluSerLeu
AGGTTTAAAAGGATCTCGCTTTGATATACCAATATTAGAATCTTTA
     3070      3080      3090      3100

SerLysSerAlaLysLysLeuGlnGlnArgThrGlnAlaAsnLys
CTCAAAATCAGCTAAGAAACTTCAACAGAGAACCCAGGCTAATAAA
     3160      3170      3180      3190

GluTyrLeuGlySerSerGluGlnMetAsnSerIleThrTyrAsn
AGAATATTTAGGAAGTAGTGAACAAATGAATTCAATAACATACAAT
     3250      3260      3270      3280

AsnIleSerAspLeuSerTyrThrAspGlnLysGluIleLeuGlu
AAATATTTCAGATTTAAGTTATACAGATCAGAAGGAAATATTAGAA
     3340      3350      3360      3370

AsnThrAlaLeuAsnAlaAlaGluGlnLeuLeuSerAspAsnSer
GAACACAGCTTTAAATGCCGCTGAACAATTGTTGTCAGATAATTCA
     3430      3440      3450      3460

LeuSerSerIleMetGluArgTyrAlaGlyGlyLysArgAsnAsp
ATTATCATCCATTATGGAGAGATATGCAGGTGGTAAAAGAAACGAT
     3520      3530      3540      3550
```

*Fig. 1(C).a.*

```
ThrLeuTyrTyrAspIleLeuGlyValGlyValAsnAlaAspMet
ACATTATATTACGATATATTAGGTGTTGGTGTTAATGCTGATAT
2570      2580      2590      2600      2610

ProTyrGlnArgSerGlySerThrValPheHisAsnPheArgLys
CCATACCAAAGATCAGGTTCTACTGTTTTCCACAACTTTAGGAA
2660      2670      2680      2690      2700

TrpTyrAsnLysTyrGlyTyrAspGlyIleLysGlnValAsnPhe
TGGTACAATAAATACGGATATGATGGAATAAAACAAGTCAACTT
2750      2760      2770      2780      2790

LysAspPheThrGlyThrProGlnIleValThrLeuLeuArgPhe
AAAGATTTTACCGGAACACCCCAAATAGTAACTCTTTTGAGATT
2840      2850      2860      2870      2880

GluHisLeuLeuLysPheMetGluGlnTyrGlnLysGluArgGlu
GAACATTTATTAAAATTTATGGAACAATATCAAAAAGAAAGAGA
2930      2940      2950      2960      2970

AlaGlyAspSerLysTrpAsnValProIleIleThrLysLeuGlu
GCTGGTGATTCAAAATGGAATGTACCAATTATAACAAAACTTGA
3020      3030      3040      3050      3060

ArgTrpIlePheLysHisValAlaLysThrHisLeuLysLysSer
AGATGGATATTCAAACATGTCGCTAAAACACATTTGAAAAAATC
3110      3120      3130      3140      3150

GlnGluLeuAlaAsnIleAsnAsnAsnLeuMetSerThrLeuLys
CAAGAATTAGCAAATATAAATAATAACCTAATGAGTACATTGAA
3200      3210      3220      3230      3240

PheGluAsnIleAsnSerAsnValAspAsnGlyAsnGlnSerLys
TTCGAAAACATCAATTCCAATGTTGATAACGGAAACCAATCAAA
3290      3300      3310      3320      3330

LysIleValSerTyrIleValAspIleSerLeuTyrAspIleGlu
AAAATTGTTAGTTATATAGTAGATATTTCCCTTTATGATATAGA
3380      3390      3400      3410      3420

ValAspGluLysThrLeuLysLysArgAlaGlnSerLeuLysLys
GTAGATGAAAAAACTCTTAAAAAGAGAGCTCAATCATTAAAAAA
3470      3480      3490      3500      3510

LysLysSerLysAsnPheAspThrLysAspIleValGlyTyrIle
AAAAAATCAAAAAATTTTGATACCAAAGATATTGTAGGATATAT
3560      3570      3580      3590      3600
```

FIG. I(C).b.

```
MetHisGlyIleSerThrIleAsnThrGluMetLysAsnGlnAsn
TATGCATGGAATTAGCACAATTAATACAGAAATGAAAAACCAAAAT
     3610      3620      3630      3640

GluHisAspAlaGluGluAsnValGluHisAspAlaGluGluAsn
AGAACATGATGCTGAAGAAAATGTAGAACATGATGCTGAAGAAAAT
     3700      3710      3720      3730

AsnValGluHisAspAlaGluGluAsnValGluGluAsnValGlu
AAATGTAGAACATGATGCTGAAGAAAATGTAGAAGAAAATGTTGAA
     3790      3800      3810      3820

GluAsnValGluGluValGluGluAsnValGluGluAsnValGlu
AGAAAATGTTGAAGAAGTAGAAGAAAATGTAGAAGAAAATGTAGAA
     3880      3890      3900      3910

GluGluAsnValGluGluAsnValGluGluAsnValGluGluTyr
TGAAGAAAATGTAGAAGAAAATGTAGAAGAAAATGTTGAAGAATAT
     3970      3980      3990      4000

ValGluGluAsnValGluGluAsnValGluGluAsnValGluGlu
TGTAGAAGAAAATGTTGAAGAAAATGTAGAAGAAAATGTTGAAGAA
     4060      4070      4080      4090

AsnValGluGluAsnValGluGluAsnValGluGluTyrAspGlu
GAATGTTGAAGAGAATGTTGAAGAGAATGTTGAAGAATATGATGAA
     4150      4160      4170      4180

AATATATATATTAAAGTTTTAATTTTTATAAACAGAATAATACTAA
     4240      4250      4260      4270

TATGAAAAAGAAATGTGTGTTTTTTTTCTTTTTTTTTTTTTTTTT
     4330      4340      4350      4360

ATTTATTTCTTTTAATTTGCGATATGATATTACATGTAAATAATAA
     4420      4430      4440      4450

CATTGTAATTTATATTGTTGTATTTGTTTTAATGTTTTCACATTTT
     4510      4520      4530      4540

```
       GluAsnValProGluHisValGlnHisAsnAlaGluGluAsnVal
       GAAAATGTACCAGAACATGTACAACATAATGCTGAAGAAAATGT
       3650      3660      3670      3680      3690

ValGluHisAspAlaGluGluAsnValGluHisAspAlaGluGlu
       GTAGAACATGATGCTGAAGAAAATGTAGAACATGATGCTGAAGA
       3740      3750      3760      3770      3780

GluValGluGluAsnValGluGluAsnValGluGluAsnValGlu
       GAAGTAGAAGAAAATGTAGAAGAAAATGTAGAAGAAAATGTAGA
       3830      3840      3850      3860      3870

GluAsnValGluGluAsnValGluGluAsnValGluGluAsnVal
       GAAAATGTAGAAGAAAATGTTGAAGAAAATGTTGAAGAAAATGT
       3920      3930      3940      3950      3960

AspGluGluAsnValGluGluValGluGluAsnValGluGluAsn
       GATGAAGAAAATGTTGAAGAAGTAGAAGAAAATGTAGAAGAAAA
       4010      4020      4030      4040      4050

ValGluGluAsnValGluGluAsnValGluGluAsnValGluGlu
       GTAGAAGAAAATGTAGAAGAAAATGTAGAAGAAAATGTAGAAGA
       4100      4110      4120      4130      4140

GluAsnValGluGluHisAsnGluGluTyrAspGlu
       GAAAATGTTGAAGAACACAATGAAGAATATGATGAATAAAAAAA
       4190      4200      4210      4220      4230

ATGAACGATTTCTCTTTATGAAAATAAAATATTTAAAACAGATA
       4280      4290      4300      4310      4320

TTTTCTTGCATGAATGTATTTGTTATTTTAAAATTTGTTCTTAT
       4370      4380      4390      4400      4410

TTTGTAATTTATATTTTTTCTTTTCTTTTTATTTTTATTTTATT
       4460      4470      4480      4490      4500

ATTTGTCTTTTTTTTATTATAATTAAAAAAAAAAAAAACGGAATT
       4550      4560      4570      4580      4590
```

*FIG. 1(D).b.*

```
               AAATATAAGTGTATATAAAAAAAAATATAATCATATTTTTTTTATT
                  10        20        30        40

GlnAsnLysAlaSerSerProSerIleAsnValAspGluTyrSe
             CACAAAATAAAGCTTCTAGTCCAAGCATAAATGTAGATGAATATTC
                 100       110       120       130

ThrAsnLeuThrProAspGlnIleSerAlaLeuAsnAlaHisLe
             TTACGAATCTAACACCTGATCAAATAAGTGCATTGAATGCGCATTT
                 190       200       210       220

AsnAsnGluAsnGluValAsnProLeuValProSerSerIleSe
             CAAATAACGAAAATGAAGTAAATCCATTAGTACCATCATCAATTTC
                 280       290       300       310

IleSerIleValAsnPheCys
             TTATTTCTATTGTTAATTTTTGTGTAAGGAAAATAAAATAAAATAA
                 370       380       390       400

AATATTCATGTATAAAATAATTTTAACCTATCATACATGTTTTAAT
                 460       470       480       490

ArgLysLysSerGlnThrTyrAsnLys
             TTTTATATTTTTTCTTTAGCGAAAGAAATCACAAACATACAATAAA
                 550       560       570       580

AlaThrGlnGlnGluAsnSerAsnGlnAsnLysGluIleAsnGlu
             TGCAACACAGCAAGAAAATAGTAATCAAAATAAGGAAATTAATGAA
                 640       650       660       670

ThrValThrThrGlnAlaAlaAlaThrProGlnGluThrValGlu
             AACAGTCACAACACAAGCAGCAGCCACACCACAAGAAACAGTCGAA
                 730       740       750       760

ProValThrThrGlnGluProIleThrValGlnGluProValThr
             ACCTGTAACAACACAAGAACCTATAACGGTACAAGAACCAGTCACA
                 820       830       840       850

ProValThrValGlnGluProValThrValGlnGluProValThr
             ACCAGTCACAGTACAAGAACCAGTCACAGTACAAGAACCAGTCACA
                 910       920       930       940
```

*FIG. 7(A).a.*

```
                                                          MetGluSer
TTGTTCTTGATACCTTACAATAGTATATAATATAGAAATGGAAT
     50        60        70        80        90 rSerLeuThrSerAsnAsnGluAsnProGlnAsnThrAlaThrLeu
AAGTCTTACAAGCAACAATGAAAATCCACAAAATACCGCTACTC
    140       150       160       170       180 uProAsnGluIleAsnIleGluThrIleThrSerThrLeuThrThr
ACCAAATGAAATAAATATAGAAACAATTACTTCTACATTGACAA
    230       240       250       260       270 rAsnThrLeuAspThrLeuThrPheTyrGlnLeuIleLeuIleIle
AAATACCCTAGATACATTGACATTTTATCAATTAATTTTGATAA
    320       330       340       350       360

ATATTAATAATAATCATAATAATAATAAATGTTATATAATAAAA
    410       420       430       440       450

TATACATATTCATTATAATATTGTAAATATTTATATTCATATAT
    500       510       520       530       540

AsnPheGluGluLysPheAsnLeuAlaSerValGlnSerSerAsn
AATTTTGAAGAAAAATTTAATTTAGCAAGCGTTCAAAGTTCTAA
    590       600       610       620       630

ValLysGluSerSerGlnThrGlnProProValThrProGlnGlu
GTAAAAGAGTCTTCTCAAACACAACCACCAGTGACACCACAAGA
    680       690       700       710       720

ThrGlnGluProValThrIleGluGluProValThrThrGlnGlu
ACACAAGAACCAGTAACAATAGAAGAACCAGTAACAACACAAGA
    770       780       790       800       810

ValGlnGluProValThrValGlnGluProValThrValGlnGlu
GTACAAGAACCAGTCACAGTACAAGAACCAGTCACAGTACAAGA
    860       870       880       890       900

ValGlnGluProValThrSerGlnGluProValThrProGlnGlu
GTACAAGAACCTGTGACATCACAAGAACCTGTGACACCACAAGA
    950       960       970       980       990
```

*Fig. 7(A).b.*

```
ProValThrProGlnGluProValThrProGlnGluProValThr
ACCTGTGACACCACAAGAACCTGTGACACCACAAGAACCTGTGACA
    1000        1010        1020        1030

ProValThrIleGluGluProValThrThrGlnGluProValThr
ACCAGTAACAATAGAAGAACCAGTAACAACACAAGAACCAGTAACA
    1090        1100        1110        1120

ProValThrThrGlnGluProValThrThrGlnGluProValThr
ACCAGTAACAACACAAGAACCAGTAACAACACAAGAACCAGTAACA
    1180        1190        1200        1210

ProValThrValGluGluHisIleAspGluLysLysGlySerGlu
ACCAGTAACAGTAGAAGAACATATTGATGAGAAAAAAGGATCAGAA
    1270        1280        1290        1300

LysSerHisThrLysLysLysLysSerSerTrpLeuLysPheGly
AAAATCTCACACAAAAAAAAAAAAAAGCAGCTGGCTTAAATTTGGA
    1360        1370        1380        1390

SerLeuGluSerValLysGlnAsnAlaAspGluGlnLysGluGln
TTCATTAGAAAGTGTAAAACAAAATGCTGATGAACAAAAAGAACAA
    1450        1460        1470        1480

IleGlnGluProThrAlaThrGlnGluProProThrThrGlnGlu
AATACAAGAACCAACCGCAACACAAGAACCACCCACAACACAAGAA
    1540        1550        1560        1570

GluGlnGluProThrThrThrGlnGluThrValThrAlaGlnGlu
AGAACAAGAACCAACAACAACACAAGAAACAGTAACAGCACAAGAA
    1630        1640        1650        1660

ThrGlnGluLeuIleAlaThrGlnGluProSerThrThrGlnGlu
AACACAAGAACTAATCGCAACACAAGAACCATCCACAACACAAGAA
    1720        1730        1740        1750

SerArgLeuSerGluGluThrGluGluLysSerHisThrLysLys
AAGCAGATTATCGGAAGAAACTGAAGAAAAAATCTCACACAAAAAAA
    1810        1820        1830        1840
```

*FIG. 7(B).a.*

```
ProGlnGluProValThrThrGlnGluProValThrThrGlnGlu
CCACAAGAACCAGTAACAACACAAGAACCAGTAACAACACAAGA
1040      1050      1060      1070      1080

IleGluGluProValThrThrGlnGluProValThrIleGluGlu
ATAGAAGAACCAGTAACAACACAAGAACCAGTAACAATAGAAGA
1130      1140      1150      1160      1170

ThrGlnGluProValThrThrGlnGluProValThrThrGlnGlu
ACACAAGAACCAGTAACAACACAAGAACCAGTAACAACACAAGA
1220      1230      1240      1250      1260

GlyAspAsnIleSerLeuSerSerLeuSerGluGluThrGluGlu
GGTGATAACATTTCATTAAGCAGCTTATCGGAAGAAACTGAAGA
1310      1320      1330      1340      1350

ArgGlyAsnLysAsnAspLysLysSerLysAsnGluLysLysPro
AGAGGAAATAAAAATGACAAAAAAAGTAAAAACGAAAAAAAACC
1400      1410      1420      1430      1440

ProThrAspSerGlnIleSerValAsnAlaGlnAspSerValThr
CCTACAGATTCACAAATATCTGTTAATGCGCAAGATTCAGTAAC
1490      1500      1510      1520      1530

LeuThrAlaThrGlnGluProThrThrThrGlnGluThrValThr
CTAACCGCAACACAAGAACCAACCACGACACAAGAAACAGTAAC
1580      1590      1600      1610      1620

ProIleThrThrGlnGluProValThrAlaGlnGluProValThr
CCTATAACTACGCAAGAACCTGTTACAGCTCAAGAACCAGTCAC
1670      1680      1690      1700      1710

HisAlaAspGluLysLysAlaSerGluGlyAspAsnIleSerLeu
CATGCTGATGAGAAGAAAGCATCAGAAGGTGATAACATTTCATT
1760      1770      1780      1790      1800

LysLysSerSerTrpLeuLysPheGlyArgGlyAsnLysAsnAsp
AAAAAAAGCAGCTGGCTTAAATTTGGAAGAGGAAATAAAAATGA
1850      1860      1870      1880      1890
```

*FIG. 7(B).b.*

```
         LysLysSerLysAsnGluLysLysProSerLeuGluSerValLys
         CAAAAAAAGTAAAAACGAAAAAAAACCTTCATTAGAAAGTGTAAAA
              1900      1910      1920      1930

SerValAsnAlaGlnAspSerValThrIleGlnGluProThrAla
         ATCTGTTAATGCGCAAGATTCAGTAACAATACAAGAACCAACCGCA
              1990      2000      2010      2020

ProThrThrThrGlnGluThrValThrGluGlnGluProThrThr
         ACCAACCACGACACAAGAAACAGTAACAGAACAAGAACCAACAACA
              2080      2090      2100      2110

ProValThrAlaGlnGluProValThrThrGlnGluLeuIleAla
         ACCTGTTACAGCTCAAGAACCAGTCACAACACAAGAACTAATCGCA
              2170      2180      2190      2200

AlaSerGluGlyAspAsnIleSerLeuSerArgLeuSerGluGlu
         AGCATCAGAAGGTGATAACATTTCATTAAGCAGATTATCGGAAGAA
              2260      2270      2280      2290

LysPheGlyArgGlyAsnLysAsnAspLysLysSerLysAsnGlu
         TAAATTTGGAAGAGGAAATAAAAATGACAAAAAAAGTAAAAACGAA
              2350      2360      2370      2380

LysGluGlnProThrAspSerGlnIleSerValAsnAlaGlnAsp
         AAAAGAACAACCTACAGATTCACAAATATCTGTTAATGCGCAAGAT
              2440      2450      2460      2470

ThrGlnGluLeuThrAlaThrGlnGluProThrThrThrGlnGlu
         AACACAAGAACTAACCGCAACACAAGAACCAACCACGACACAAGAA
              2530      2540      2550      2560

AlaGlnGluProIleThrThrGlnGluProValThrAlaGlnGlu
         AGCACAAGAACCTATAACTACGCAAGAACCTGTTACAGCTCAAGAA
              2620      2630      2640      2650

ThrGlnGluHisAlaAspGluLysLysAlaSerGluGlyAspAsn
         AACACAAGAACATGCTGATGAGAAGAAAGCATCAGAAGGTGATAAC
              2710      2720      2730      2740
```

*FIG. 7(C)a.*

```
GlnAsnAlaAspGluGlnLysGluGlnProThrAspSerGlnIle
CAAAATGCTGATGAACAAAAAGAACAACCTACAGATTCACAAAT
1940      1950      1960      1970      1980

ThrGlnGluProProThrThrGlnGluLeuThrAlaThrGlnGlu
ACACAAGAACCACCCACAACACAAGAACTAACCGCAACACAAGA
2030      2040      2050      2060      2070

ThrGlnGluThrValThrAlaGlnGluProIleThrThrGlnGlu
ACACAAGAAACAGTAACAGCACAAGAACCTATAACTACGCAAGA
2120      2130      2140      2150      2160

ThrGlnGluProSerThrThrGlnGluHisAlaAspGluLysLys
ACACAAGAACCATCCACAACACAAGAACATGCTGATGAGAAGAA
2210      2220      2230      2240      2250

ThrGluGluLysSerHisThrLysLysLysLysSerSerTrpLeu
ACTGAAGAAAAATCTCACACAAAAAAAAAAAAAAGCAGCTGGCT
2300      2310      2320      2330      2340

LysLysProSerLeuGluSerValLysGlnAsnAlaAspGluGln
AAAAAACCTTCATTAGAAAGTGTAAAACAAAATGCTGATGAACA
2390      2400      2410      2420      2430

SerValThrIleGlnGluProThrAlaThrGlnGluProProThr
TCAGTAACAATACAAGAACCAACCGCAACACAAGAACCACCCAC
2480      2490      2500      2510      2520

ThrValThrGluGlnGluProThrThrThrGlnGluThrValThr
ACAGTAACAGAACAAGAACCAACAACAACACAAGAAACAGTAAC
2570      2580      2590      2600      2610

ProValThrThrGlnGluLeuIleAlaThrGlnGluProSerThr
CCAGTCACAACACAAGAACTAATCGCAACACAAGAACCATCCAC
2660      2670      2680      2690      2700

IleSerLeuSerArgLeuSerGluGluThrGluGluLysSerHis
ATTTCATTAAGCAGATTATCGGAAGAAACTGAAGAAAAATCTCA
2750      2760      2770      2780      2790
```

*FIG. 7(C).b.*

```
   Thr Lys Lys Lys Lys Ser Ser Trp Leu Lys Phe Gly Arg Gly Asn
   CACAAAAAAAAAAAAAAAGCAGCTGGCTTAAATTTGGAAGAGGAAAT
       2800        2810        2820        2830
```

```
   Ser Val Lys Gln Asn Ala Asp Glu Gln Lys Glu Gln Pro Thr Asp
   AAGTGTAAAACAAAATGCTGATGAACAAAAAGAACAGCCTACAGAT
       2890        2900        2910        2920
```

```
   Pro Ile Thr Ala Gln Glu Thr Val Thr Asp Gln Glu Pro Ile Thr
   ACCTATTACAGCTCAAGAAACTGTTACAGATCAAGAACCTATAACA
       2980        2990        3000        3010
```

```
   Thr Val Thr Ser Leu Val Pro Asn Arg Asn Thr Arg Asn Ser Asn
   AACGGTTACTTCTCTTGTTCCGAATCGCAACACAAGAAACAGTAAC
       3070        3080        3090        3100
```

```
   Pro Val Thr Ala Gln Glu Pro Val Thr Thr Gln Glu
   ACCTGTTACAGCTCAAGAACCAGTGACAACACAAGAA
       3160        3170        3180
```

FIG. 7(D).a.

```
   Lys Asn Asp Lys Lys Ser Lys Asn Glu Lys Lys Pro Ser Leu Glu
   AAAAATGACAAAAAAAGTAAAAACGAAAAAAAACCTTCATTAGA
       2840        2850        2860        2870        2880
```

```
   Ser Gln Ile Ser Val Asn Ala Gln Asp Ser Val Thr Thr Gln Glu
   TCACAAATATCTGTTAATGCACAAGATTCAGTAACAACTCAAGA
       2930        2940        2950        2960        2970
```

```
   Thr Glu Glu Pro Leu Thr Thr Gln Glu Thr Val Thr Thr Gln Glu
   ACTGAAGAACCCTTAACCACACAAGAAACGGTTACAACACAAGA
       3020        3030        3040        3050        3060
```

```
   Arg Thr Arg Thr Ile Thr Thr Gln Glu Pro Ile Thr Thr Gln Glu
   AGAACAAGAACTATAACGACACAGGAACCTATAACGACACAAGA
       3110        3120        3120        3140        3150
```

THE RESA AND FIRA ANTIGENS OF *PLASMODIUM FALCIPARUM*

This is a continuation of application Ser. No. 06/862,357 filed as PCT/AU85/00223, Sep. 10, 1985, now abandoned.

This invention relates to synthetic peptides and polypeptides which have antigenicity suitable for providing protective immunity against *Plasmodium falciparum* infections, and to methods for the production thereof.

Immunity to *Plasmodium falciparum*, the protozoan causing the most severe form of human malaria, is acquired only after extensive exposure over a number of years. A large number of *P. falciparum* polypeptides are natural immunogens in man but it is by no means clear how many are important in protective immunity. Many antigens may have no such role, and indeed it is possible that some are counterproductive, perhaps because collectively they overload the immune system. Antigenic diversity among different strains of the parasite may also play a significant role in the process of immune evasion as a number of *P. falciparum* antigens that are strain-specific have been identified.

Recently, molecular cloning techniques have facilitated the analysis of individual polypeptide antigens of *P. falciparum* (1). Many cDNA clones encoding these antigens have been isolated by screening *Escherichia coli* colonies that express the cloned sequences with human antibodies. The production and screening of these clones is described below.

One such antigen has been located at the surface of erythrocytes infected with the immature ring stage of *P. falciparum* and hence has been designated the Ring-infected Erythrocyte Surface Antigen (RESA). Because of this exposed location, it appears to be a likely target for immune attack. RESA shows the structural peculiarity that has now been found in a number of *Plasmodium* antigens, namely multiple tandem repeats of oligopeptides (2-6).

Studies by hybridization and by immunofluorescence suggest that RESA from the Papua New Guinea isolate FC27, may be conserved in a wide range of *P. falciparum* isolates, including strain NF7 from Ghana. The relationship between RESA cDNA clones from two different strains of *P. falciparum* has therefore been studied by immunological and sequencing methods. Antibodies that reacted with RESA from strain FC27 of Papua New Guinea were present in patients from Africa and conversely, antibodies that reacted with RESA from strain NF7 were present in patients from Papua New Guinea. From the complete nucleotide sequences of eight cDNA clones encoding portions of RESA from *P. falciparum* strains FC27 and NF7, it is concluded that the RESA polypeptides from the two strains are closely homologous. The sequencing of these cDNA clones identified in the RESA polypeptide two separate blocks of tandem sequence repeats. One block of repeats, located at the C terminus of RESA in FC27, contains four different but related acidic sequences of eight, four, four and three amino acids. Approximately 600 bases 5' is a second block of repeats encoding related amino acid sequences which are also rich in acidic amino acids. Consistent with the sequence relationships, the two blocks of repeats have been shown to encode cross-reacting antigenic epitopes.

Immunoblots on the antigens of synchronously growing parasites separated on SDS-PAGE suggested that RESA is synthesized in the mature trophozoite as a Mr 210,000 protein which is processed to the Mr 155,000 form found bound to the membrane of erythrocytes infected with ring stage parasites. The more recent finding that the Mr 210,000 protein does not react with several anti-RESA monoclonal antibodies and anti-RESA peptide antibodies suggests that the Mr 210,000 protein is a cross-reacting antigen and not a precursor of the Mr 155,000 RESA molecule.

The Mr 155,000 polypeptide in merozoites is soluble in the non-ionic detergent Triton X-100 but after transfer to the membrane of the ring-infected erythrocyte it is largely Triton-insoluble. Thus, it seems likely that RESA interacts with the erythrocyte cytoskeleton. Whether RESA penetrates the membrane lipid bilayer is not yet clear, but an important clue may come from the complete sequence of the RESA gene which has now been determined. From this, it is deduced that RESA contains two exons separated by a short intervening sequence (FIG. 2). Exon 1 commences with a hydrophobic sequence typical of signal peptides on secreted polypeptides in many organisms. Following this, there is a hydrophilic sequence of approximately 36 amino acid residues and then a second hydrophobic stretch, of 14 residues. 202 bases further downstream exon 2 commences with a 16 amino acid non-charged sequence and then continues with a highly charged region. The hydrophobic sequence generated by excision of the intron is typical of membrane-anchor segments in a number of eukaryotic genes.

As a result of work leading to the present invention, described in detail below, it has been shown on the basis of sequence, hybridization and immunological data that it is likely that RESA is highly conserved in most or all strains of *P. falciparum*. In addition, as the repetitive structure and the location of RESA at the surface of ring infected erythrocytes are properties highly suited for sensitive detection by such procedures as indirect immunofluorescence, the high degree of immunological similarity of RESA in different strains suggest that RESA is a molecule well suited for immunodiagnostic purposes.

Another antigen detected as a result of its cloning and expression in *E. coli* has been designated the Falciparum Interspersed Repeat Antigen (FIRA) (6). Like some other repetitive antigens FIRA contains a structural unit bearing repeats of a short unit flanked by a highly charged region. However, this entire structural unit is itself repeated several times within the antigen.

The corresponding cDNA clone expressing FIRA in *Escherichia coli* reacted in an in situ colony assay with sera from up to ~93% of people living in an area endemic for *P. falciparum*. Human antibodies affinity-purified on immobilized lysates of the corresponding cDNA clone identified the corresponding parasite antigen as a polypeptide of Mr >300,000. It was present in schizonts and also in ring-stage trophozoites, where a speckled immunofluorescence pattern suggested an association with the erythrocyte. Its mRNA was enriched in merozoites, a distinctive property shared by RESA which is located on the surface of ring-infected erythrocytes and it is encoded by a single gene with a number of allelic variants. The complete nucleotide sequence of the cDNA clone revealed a structural unit comprised of 13 hexapeptide repeats flanked by a highly charged region containing both acidic and basic amino acids. This structural unit is itself repeated, so that blocks of repeats and charged units are interspersed along the molecule.

The sequence within the repeats vary much more extensively than those in the charged units.

The sequence of a chromosomal FIRA clone demonstrates that the FIRA gene is organised in a manner analogous to that of RESA (FIG. 8). It contains a short 5' exon, a much longer 3' exon and a hydrophobic segment at the boundary of the two exons. As with RESA, the repeats in FIRA are restricted to the 3' exon only.

According to the present invention, there is provided a DNA molecule comprising a nucleotide sequence substantially corresponding to all or a portion of the base sequence coding for an antigen of P. falciparum selected from the group consisting of the Ring-infected Erythrocyte Surface Antigen (RESA), the Falciparum Interspersed Repeat Antigen (FIRA), and other antigens of P. falciparum cross-reactive therewith. In particular, there is provided a DNA molecule comprising a nucleotide sequence characterised by at least a portion thereof comprising all or a portion of the base sequence shown in FIG. 1 or FIG. 7. Such a nucleotide sequence codes for a polypeptide comprising at least a portion which corresponds to the amino acid sequence of RESA or FIRA.

As noted above, and set out in greater detail in FIG. 1 and 7, the amino acid sequences of RESA and FIRA consist of repeat units and flanking non-repeat peptide units. Accordingly, the base sequences referred to above may code for polypeptides corresponding to one or more of these repeat and/or flanking units, or to polypeptides corresponding to combinations of these repeat and/or flanking units.

The present invention also extends to synthetic peptides or polypeptides displaying the antigenicity of all or a portion of an antigen selected from the group consisting of the RESA antigen, the FIRA antigen, and other antigens of P. falciparum which are cross-reactive therewith, as well as to compositions for stimulating immune responses against P. falciparum in a mammal, which compositions comprise at least one synthetic peptide or polypeptide as described above, together with a pharmaceutically acceptable carrier therefor. The synthetic peptides or polypeptides according to this aspect of the invention may be prepared by expression in a host cell containing a recombinant DNA molecule which comprises a nucleotide sequence as broadly described above operatively linked to an expression control sequence, or a recombinant DNA cloning vehicle or vector containing such a recombinant DNA molecule. The synthetic peptide or polypeptide so expressed may be a fusion polypeptide comprising a portion displaying the antigenicity of all or a portion of RESA or FIRA or other cross-reactive antigen, and an additional polypeptide coded for by the DNA of the recombinant DNA molecule fused thereto. Alternatively, the synthetic peptides or polypeptides may be produced by chemical means, such as by the well-known Merrifield solid-phase synthesis procedure.

Further details of the present invention will be apparent from the detailed description hereunder, and from the accompanying Figures. In the Figures:

FIG. 1 shows the nucleotide sequence and predicted amino acid sequence of RESA. The nucleotide sequence was determined by the dideoxy procedure (8).

FIG. 3 shows: A. Western blot of asynchronous cultures of two isolates of P. falciparum lysed in electrophoresis sample buffer and probed with anti-RESA antibodies. B. & C. Western blots of P. falciparum (1) ring stages, (2) mature trophozoites, (3) schizonts, and (4) merozoites using affinity-purified human antibodies to RESA. (B) Antigens extracted in Triton X-100. (C) Antigens insoluble in Triton X-100 but soluble in electrophoresis sample buffer. Radioactive molecular weight markers were obtained from Amersham Internat., Buckinghamshire, England and were myosin (200 Kdaltons), phosphorylase-b (93 Kdaltons) and bovine serum albumin (69 Kdaltons).

Figure 4:

FIG. 4 is an immunoelectronmicrograph showing the location of RESA (→) in small dense vesicles presumably micronemes within the developing merozoites in a schizont, detected with rabbit anti-RESA and protein A gold. The rhoptries (R) are unlabelled. ($\times$41,700; inset$\times$73,000).

Figure 5:

FIG. 5 is an immunoelectronmicrograph showing a section of a ring-infected erythrocyte reacted with rabbit anti-RESA. Also shown is part of an uninfected erythrocyte.

Figure 6:
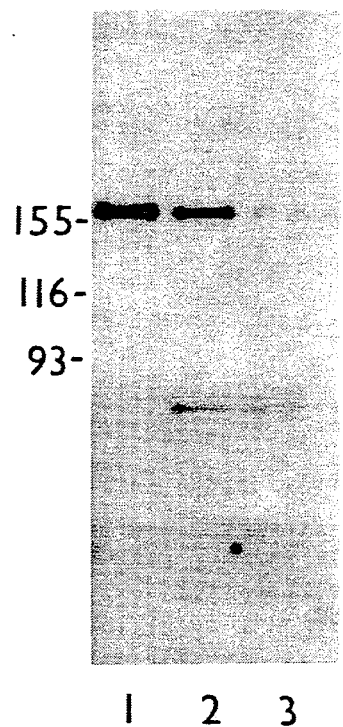

FIG. 6 is a Western blot of ring-stage infected erythrocytes digested with chymotrypsin (20 $\mu$g/ml) for 0 min. (1), 20 min. (2) and 60 min. (3). Subsequent to enzyme digestion the intact erythrocytes were washed, lysed in electrophoresis sample buffer, electrophoresed on a 10% SDS-polyacrylamide gel and then electrophoretically transferred to nitrocellulose. The nitrocellulose filters were then probed with rabbit anti-RESA at a dilution of 1:500. Molecular weights are indicated in Kdaltons, and correspond to RESA (155 Kd), $\beta$-galactosidase (116 Kd) and phosphorylase-b (93 Kd).

FIG. 7 shows the nucleotide sequence and predicted amino acid sequence of the FIRA gene. The nucleotide sequence was determined by the dideoxy procedure (8). The EcoRl linker ligated to the 3' end during construction of the library was absent and so the sequence is incomplete at the 3' end, perhaps due to a deletion.

Figure 8:
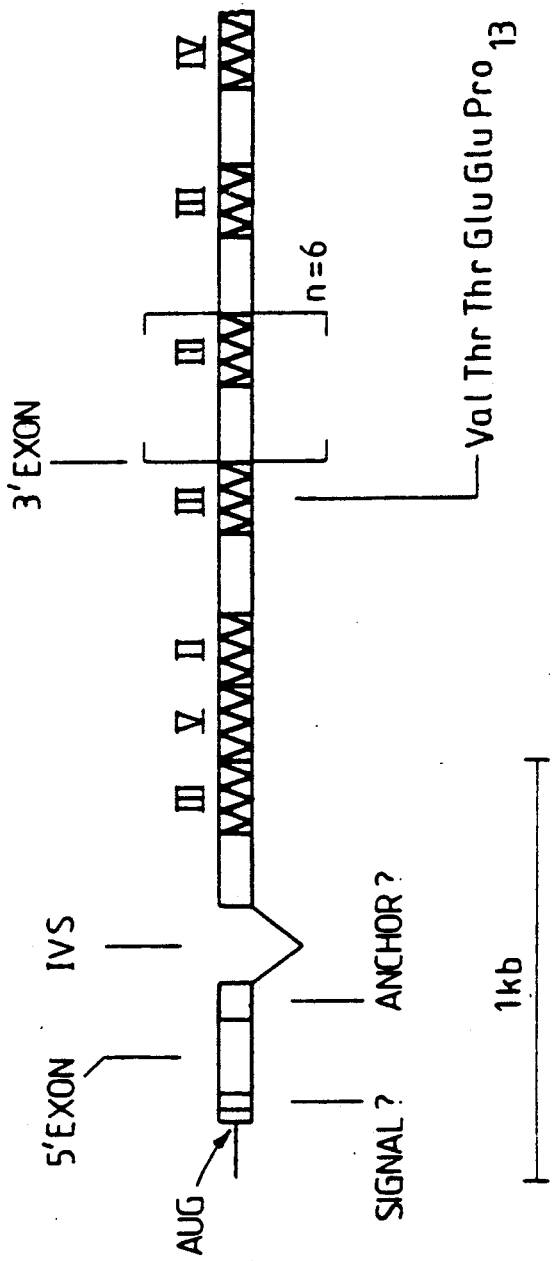

FIG. 8 shows the structure of the FIRA gene as deduced from the sequence given in FIG. 7.

FIG. 9 shows immunoassays (A & B) and Western blots (C & D) with human antibodies affinity-purified from a serum pool derived from individuals exposed to malaria. In A and C the antibodies were purified on a FIRA-Sepharose absorbent whereas in B & D the antibodies were purified on an $\lambda$amp3-Sepharose absorbent. The P. falciparum isolates in C and D were: 1, FC27 from Papua New Guinea; 2, K1 from Thailand; and 3, NF7 from Ghana.

Figure 10:
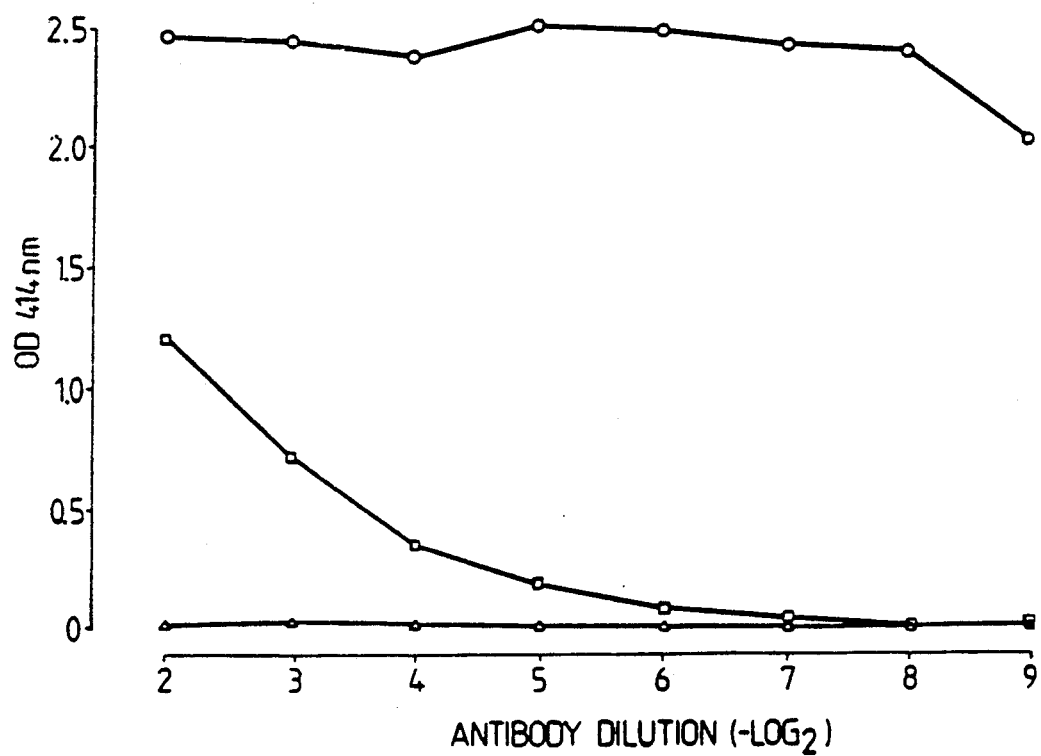

FIG. 10 shows affinity purified anti-FIRA antibodies assayed by solid-phase ELISA using microtitre plates coated with purified fusion polypeptides (2 $\mu$g/ml) corresponding to: , a fragment of FIRA; □, 5' repeat by RESA; Δ, 3' repeat of RESA.

DETAILED DESCRIPTION OF THE INVENTION

MATERIALS AND METHODS

P. falciparum isolates

Isolates FCQ27/PNG (FC27), IMR143/PNG (IMR143), IMR144/PNG (IMR144) and MAD71/PNG (MAD71) were obtained through collaboration with the Papua New Guinea Institute of Medical Research. NF7, originating from Ghana, and K1 originating from Thailand were obtained from D. Walliker, Edinburgh University.

Colony Immunoassays

Replicas of arrays of antigen-positive clones were grown overnight at 30° C., induced at 38° C., and lysed (7). Sera were absorbed to remove anti-*E.coli* reactivity, diluted 1:500 at pH 9.6 in 3% bovine serum albumin and finally incubated with $^{125}$I protein A from *Staphylococcus aureus* and autoradiographed overnight (7).

Sera

Sera were obtained with informed consent from individuals from Madang, Papua New Guinea. Some patients presented with acute malaria while in others, asymptomatic parasitemia was detected in the course of routine surveys. Parasitemic individuals were treated with chloroquine. Parental consent was obtained before taking samples from children.

Hybridization Experiments

The phage DNA was purified by CsCl-equilibrium density centrifugation, digested with EcoRI, and size-fractionated on a 1% low-melting agarose-gel, recovered by phenol extraction and labelled by nick-translation. 3 ml of labelled insert ($3 \times 10^5$ cpm) in 1 ml 0.75M NaCl/0.75M Na citrate/50% formamide/50 $\mu$g ml$^{-1}$ salmon sperm DNA/10 $\mu$g ml$^{-1}$ poly (C)/0.02% Ficoll/0.02% polyvinylpyrollidone/0.02% BSA was hybridized to the array of antigen-positive clones. The inserts were subcloned in pUC-9 (9), purified and then nick-translated as described above and used in Southern blot experiments.

Isolation and Sequencing of Cloned Chromosomal Segments

The chromosomal RESA clones were isolated from a λgt10 library, and the EcoRl inserts subcloned into pUC8. Rsa I, Aha III and Ssp I fragments of the EcoRl inserts were subcloned into M13mp18 and mp19 vectors, and sequenced by the dideoxy technique (8). Synthetic primers were also used. The results were processed by the program of Staden (10). The sequence shown consists of the 3.5 Kb chromosomal EcoRl fragment, joined at the EcoRl site to that of the cDNA clone Ag 46.

The chromosomal FIRA clone was initially identified as a 6 Kb Aha III fragment in λgt10. This Aha III fragment was subcloned into pUC8. Pvu II and Rsa I fragments were then subcloned into M13mp8 and 9 vectors and sequenced by the dideoxy technique.

Affinity Purification of Anti-RESA and Anti-FIRA Antibodies

Induced cultures (50 ml) of clones Ag28, Ag231 and λamp3 were prepared as described previously (5 and 6). The pelleted bacteria were sonicated in 100 mM Na phosphate buffer, pH 6.8/10 mM dithiothreitol followed by mixing at room temperature with the addition of 1% NaDodSO$_4$. The soluble bacterial proteins were equilibrated with 100 mM Na phosphate, pH 6.8/1 mM dithiothreitol/0.1% NaDodSO$_4$ by passage through Sephadex G-10 and conjugated to CNBr-activated Sepharose (Pharmacia, Sweden) at room temperature according to the manufacturers instructions.

A pool of human sera collected from individuals living in Papua New Guinea was clarified by centrifugation, diluted with an equal volume of phosphate buffered saline (Pi/NaCl) and preabsorbed on a λamp3-Sepharose absorbent before passage over the Ag28 or Ag231 absorbent. Non-specifically bound proteins were removed by repeated wash cycles of 100 mM Na borate/500 mM NaCl/0.05% Tween 20, pH 8.5 followed by Pi/NaCl. Bound antibodies were eluted with 100 mM glycine/150 mM NaCl, pH 2.6 and immediately adjusted to pH 7.0 with 2M Tris; HCl, pH 8.0.

Western Blots

Protein extracts of cultures of *P. falciparum* were prepared and fractionated on 7.5% polyacrylamide/-NaDodSO$_4$ gels. Proteins from the gels were transferred electrophoretically to nitrocellulose, incubated in 5% non-fat milk powder in Pi/NaCl before reaction with affinity purified human antibodies. The filters were incubated with $^{125}$I-labelled protein A and autoradiographed.

Immunoelectronmicroscopy

Human antibodies affinity purified on Ag28 and Ag231 immunosorbents, or rabbit antisera raised against the fused polypeptide produced by Ag28 were used in immunoelectronmicroscopy employing the protein A-gold procedure. Samples for immunoelectronmicroscopy were fixed with 0.25% glutaraldehyde (10 min at 25° C.), diluted in 50 mM NH$_4$Cl in 0.1 M phosphate buffer, pH7.4, and then left in fresh 50 mM NH$_4$Cl in phosphate buffer for 30 min. Cells were then washed twice in phosphate buffer and dehydrated in 70% ethanol before being embedded in L. R. White resin, hard grade (London Resin Co. Ltd., Basingstoke, England). Sections were incubated in 1% bovine serum albumin or ovalbumin in 0.05M phosphate, pH7.4, containing 0.25% Tween-20 (PO$_4$:Tween) for 5 min. before transfer to a drop of rabbit anti-RESA antiserum (diluted 1:100) or affinity-purified human anti-RESA antibodies in PO$_4$:Tween for 30–60 min. at room temperature. After being washed in PO$_4$:Tween the sections were transferred to protein A-gold (E-Y Laboratories, Inc.) diluted 1:10 in PO$_4$:Tween for 30–60 min. After further washing, the sections were stained with aqueous uranyl acetate. Isolated merozoites were fixed at 4° C. in 0.25% glutaraldehyde for 10 min. and then processed in the same manner as infected cells.

RESULTS - RESA

Isolation of a RESA cDNA clone from FC27

The preparation of the RESA cDNA clones is described in detail in the Examples below.

Identification of the RESA polypeptides

Figure 2:
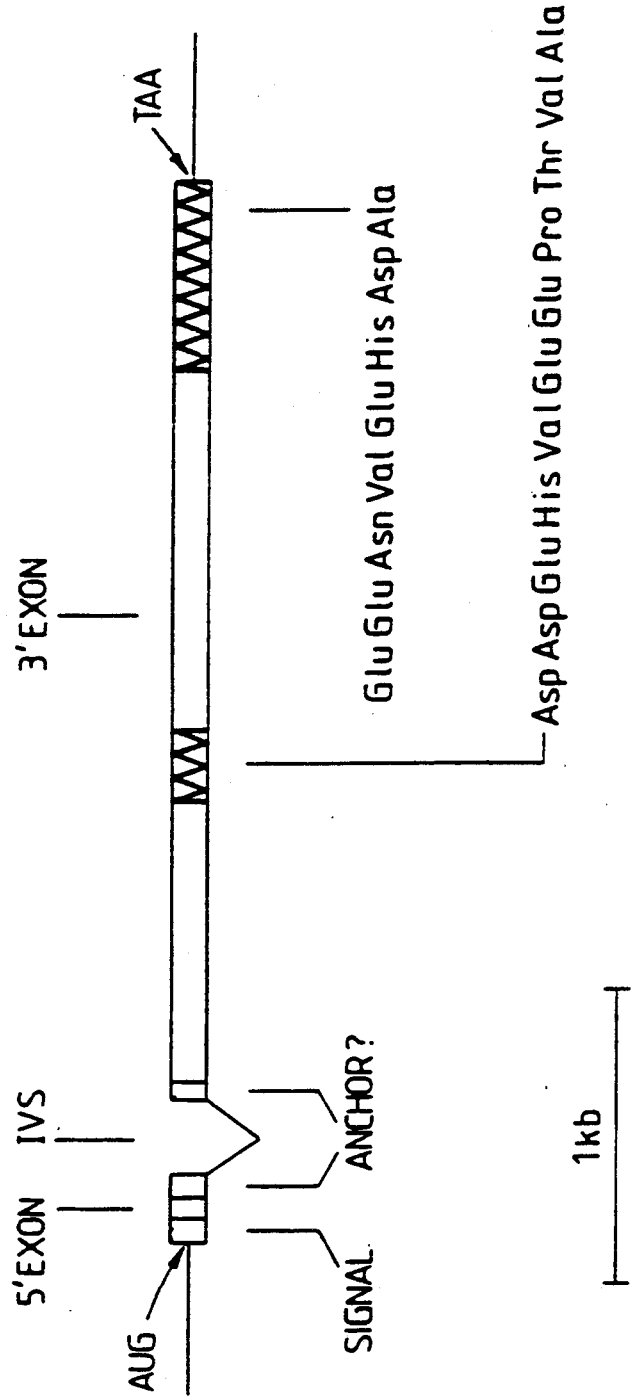
FIG. 2 shows the structure of the RESA gene, as deduced from the sequence given in FIG. 1. The 5' and 3' exons are indicated.
Figures 3A, 3B, 3C:
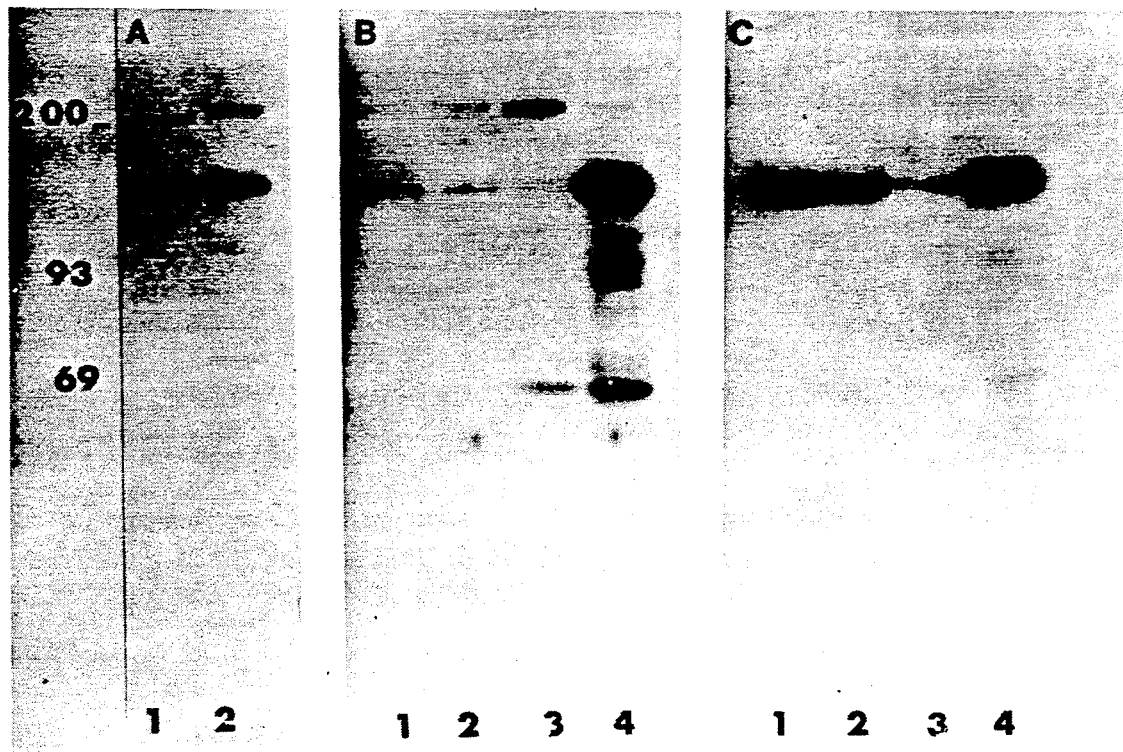

Human antibodies specific for the RESA polypeptides were purified by affinity chromatography. In Western blots the antibodies reacted with a prominent band at Mr 155,000 which, in some experiments, resolved into a closely migrating doublet. A higher molecular weight polypeptide reacting with the anti-RESA antibodies varied in size in different isolates (FIG. 3A); it was at Mr 210,000 in isolate FC27. In addition, a smaller molecular weight polypeptide (Mr 80,000) was detected in some antigen preparations (FIG. 3A). The abundance of the Mr 210,000 polypeptide was greatest in schizonts (FIG. 3B). In contrast, the Mr 155,000 antigen was abundant in the merozoites, rings and trophozoites with small amounts of schizonts (FIGS. 3, B and C.)

The solubility of RESA in detergents was determined to examine the nature of the interaction between RESA and the erythrocyte membrane. The Mr 210,000 polypeptide was soluble in solutions of the nonionic detergent Triton X-100, as was the most of the Mr 155,000 polypeptide present in merozoites (FIG. 3B). In contrast, the bulk of the Mr 155,000 antigen in rings and other life-cycle stages was insoluble in Triton X-100 but could be solubilised in electrophoresis sample buffer containing SDS and 2-mercaptoethanol (FIGS. 3, B and C).

When identical immunoblots were probed with monoclonal antibodies raised against the Ag28 fused polypeptide, or antisera raised in mice against RESA synthetic peptides, the Mr 210,000 polypeptide was not detected although the Mr 155,000 polypeptide gave a strong signal. Thus, it appears that the Mr 210,000 polypeptide is another gene product that cross-reacts with RESA and not the initial RESA translation product.

Antibodies against RESA in patients from Africa react with RESA from a Papua New Guinea strain Previous studies with mouse antibodies against RESA fused polypeptides expressed in E.coli demonstrated cross reactions with all P. falciparum strains tested, from diverse locations. These RESA cDNA clones were isolated by virtue of their reactivity to sera from Papua New Guinea. To determine whether equivalent antibodies that cross react with RESA from widely differing locations occur in humans exposed to P. falciparum, African sera were tested against a number of cDNA clones expressing portions of RESA, derived from the Papua New Guinea strain FC27. The sera were reacted with an array of 133 independently isolated antigen positive clones, 16 of which encoded RESA, by the in situ colony immunoassay procedure as described (7). Both African sera reacted with the RESA cDNA clones. The extent of reaction was quite comparable to many of the PNG sera. However, it is important to note that the extent of reaction varies considerably in different PNG sera. The African sera also reacted with a variety of other cDNA clones including cDNA clones that encode FIRA that consists largely of divergent repeats of a hexapeptide sequence. In contrast, they did not react with cDNA clones encoding the strain-specific S-antigen of FC27. Thus RESA polypeptides from geographically diverse areas must share non-reacting epitopes that are natural immunogens in man.

Antigenic determinants of RESA

All RESA cDNA expression clones previously studied immunologically were bounded at the 5' terminus by the internal EcoRl site. To examine whether any antigenic determinants were located 5' to this site, the large EcoRl fragment from NF7 AG13 was subcloned into pUC9, randomly fragmented by sonication and the fragments were recloned in λAmp3. To identify clones expressing defined regions of this fragment, the resulting clones were screened by hybridization with 3 different restriction fragments, located 5' to the repeats, spanning the repeats and 3' to the repeats, respectively. Selected clones were then examined for expression of large fused polypeptides, detectable by Coomassie blue staining after polyacrylamide gel electrophoresis of total protein extracts from the cells. Because there are multiple stop codons in all but the correct frame of the sequence, it could be concluded that such clones expressed defined fragments of RESA, 5' to any fragments that had previously been analysed for antibody binding.

Clones expressing 5' repeats were then examined by in situ colony immunoassays with sera from PNG patients with a history of exposure to P. falciparum . Some clones containing the 5' repeat segment reacted with the sera. It is concluded that there are antigenic determinants that are natural immunogens in man in the 5' RESA repeats, as well as the 3' repeats.

A 36 amino acid peptide corresponding to the sequence from residue 17 to residue 52 in exon 1 of RESA (FIG. 1) was synthesised and used to test sera from individuals exposed to malaria for antibodies to this region of RESA. Some individuals had significant levels of antibodies reactive with this peptide as measured in a solid-phase radio-immunoassay. Thus there are naturally immunogenic epitopes in exon 1 of RESA which must be encoded by non-repeat sequences.

Immunogenicity of RESA Sequences

RESA/β-galactosidase fused polypeptides were isolated from clones expressing the 3' and 5' repeats of RESA. These proteins were tested for immunogenicity by immunizing rabbits with 0.25-0.5 mg amounts of antigen together with complete Freund's adjuvant. The rabbits were boosted with similar amounts of antigen in incomplete adjuvant 4-6 weeks later. In each case, antibodies were elicited which reacted with the RESA molecule expressed in P. falciparum growing in vitro.

Three RESA synthetic peptides (Table 1) conjugated to Keyhole Limpet Haemocyanin, were used to immunize mice and the resulting antisera were assayed against each of the three peptides conjugated to bovine serum albumin, and against fused polypeptides corresponding to the 3' and 5' repeats of RESA and sonicates of infected erythrocytes. All mice immunized with these peptides produced antibodies that were reactive with the homologous peptide and the fused polypeptide containing that sequence. In addition, peptide RESA 3'-2 (EENV x4), induced antibodies that also reacted with the other 3' repeat peptide, RESA 3'-1 (EENVEHDA) which has a 5 amino acid sequence in common. The reverse, however, was not true: anti-RESA 3'-1 antibodies did not react with RESA 3'-2.

When these anti-peptide antisera were assayed on peptide-BSA conjugates there was no apparent cross-reactivity between the 5' and 3' repeats of RESA. However, assaying the same sera on fused polypeptides revealed that the peptides had induced antibodies that reacted with both repeat structures, although the reaction with the heterologous repeat was very weak in comparison to that with the homologous repeat.

The anti-peptide antisera were used to probe Western blots of infected erythrocytes. All of the antisera reacted specifically with the Mr 155,000 RESA polypeptide.

TABLE 1

Sequences and synthetic peptides corresponding to repeats in RESA

| Region of RESA | Repeat Sequences | Peptides Synthesized* |
|---|---|---|
| 3' Repeat | EENVEHDA (5)+ | RESA 3'-1 EENVEHDA |
|  | EENA (1) |  |
|  | EENV (29) | RESA 3'-2 (EENV)n n ~4 |
|  | EE-V (4) |  |
|  | EEYD (3) |  |
| 5' Repeat | -EENEEEHTV- (1) |  |
|  | DDEHVEEHT-A (1) |  |
|  | DDEHVEEPTVA (2) | RESA 5'-1 |

TABLE 1-continued

Sequences and synthetic peptides corresponding to repeats in RESA

| Region of RESA | Repeat Sequences | Peptides Synthesized* |
|---|---|---|
| | -DEHVEEPTVA (1)<br>-EEHVEEPTVA (1)<br>-EEHVEEP--A (1) | DDEHVEEPTVAY |

*The peptides were synthesized by the Merrifield solid-phase method except the RESA 5'-1 peptide was synthesized by the FMOC solid-phase synthesis methodology of Atherton et al (11) on a Kieselguhr KA resin support.
*The numbers in brackets indicate the number of times the respective sequences occur within the blocks of repeats.

Location of RESA

RESA was detected by immunoelectronmicroscopy at the membrane of erythrocytes infected with ring-stage parasites but not in association with immature parasites within the erythrocyte (FIG. 5). In contrast, the membranes of erythrocytes containing mature parasites were not labelled, but gold particles were associated with electron-dense organelles presumed to be micronemes within the parasite cytoplasm (FIG. 4). Control antibodies to S antigens did not react with merozoites or the erythrocyte membrane.

The labelling of merozoites was clearly internal, with no indication of specific labelling of the merozoite surface. Labelling occurred in clusters away from the nucleus and occasionally over a rhoptry. In other merozoites, gold particles were more dispersed but were located near the rhoptries, which were particle-free. Similar distributions of gold were observed with both affinity-purified human antibodies and rabbit antibodies raised against the cloned antigen, although higher background labelling was evident with the affinity-purified human antibodies. The specificity of the observed patterns of labelling was demonstrated by the different patterns, or by the lack of labelling when the same procedures were used with affinity-purified human antibodies or rabbit antisera to other cloned P. falciparum antigens (e.g. S antigen).

The location of RESA was further examined by studying its accessability to attack by proteolytic enzymes. When intact erythrocytes infected with ring-stage parasites (approximately 5% parasitaemia) were treated with chymotrypsin or trypsin, the Mr 155,000 polypeptide was partially cleaved at a limited number of sites generating two main fragments which like the intact molecule reacted with anti-RESA antibodies (FIG. 6). This result indicates that at least part of the RESA molecule is exposed on the external surface of the ring-infected erythrocyte.

Inhibition of Parasite Growth in Vitro

Asynchronous cultures of P. falciparum were cultured for 48 hours in the presence of affinity-purified human anti-RESA antibodies. The degree of inhibition was variable with typical results showing 20-40% inhibition compared with control cultures.

RESULTS - FIRA cDNA Clones Expressing FIRA

FIRA cDNA clones reacted with up to 93% of a set of more than 100 PNG sera from 65 individuals, varying in clinical status. Further, they gave the most intense signals with a majority of the sera, although many sera reacted strongly with additional clones.

FIRA is Encoded by a Single Polymorphic Gene

Chromosomal DNA from 5 P. falciparum isolates (FC27, IMR143, IMR144, MAD71 from Papua New Guinea, and NF7 from Ghana) was restricted with EcoRI, AhaIII and RsaI and analysed by Southern blotting. In each isolate, a single very large (>20 kb) EcoRI fragment hybridized (data not shown). In the AhaIII and RsaI digests, smaller single fragments of varying sizes hybridized, revealing that the FIRA gene was polymorphic and present in each isolate investigated. The different fragment sizes most likely represent different alleles of the FIRA gene. As at least three different alleles were detected in only 5 different isolates, the total number of alleles is presumably very large. The single fragment size in each isolate is in accord with a haploid genome in blood stage Plasmodium.

Identification of the FIRA polypeptide

Figure 9A:
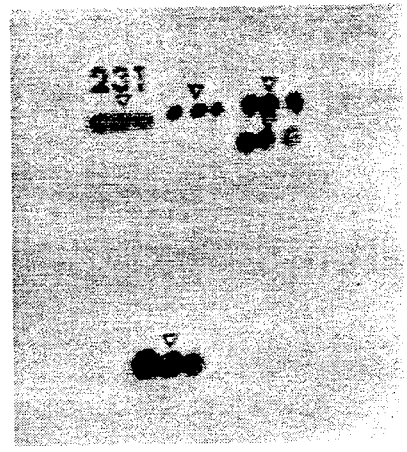
Figure 9C:
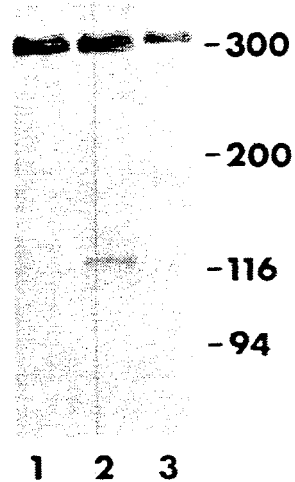
Figure 9B:
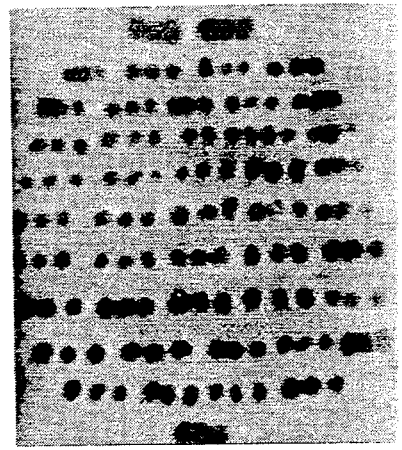
Figure 9D:
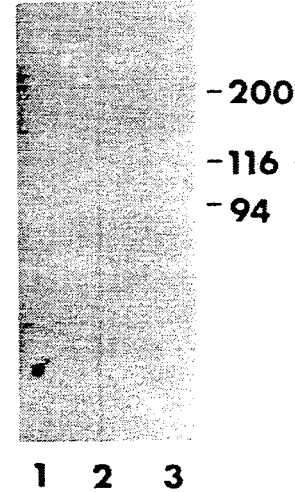

Human antibodies specific for the FIRA polypeptide (FIG. 9) were purified by affinity chromatography. In Western blots the antibodies reacted strongly with a P. falciparum polypeptide of very large apparent size, nominally of $M_r >300,000$, that was present in each isolate (FIG. 9C). Although there were no accurate size markers in this extreme range, the mobility of FIRA was considerably less than that of the Mr 200,000 S antigen of FC27. Isolate differences in the sizes of FIRA polypeptides that might be expected to correlate with the slight differences in size of the DNA fragments could not be detected (FIG. 9C). The antibodies also reacted weakly and variably with a number of smaller polypeptides (FIG. 9C), presumably proteolytic cleavage products of the $M_r >300,000$ molecule. The control antibodies, purified from the same serum on a vector absorbent did not react (FIG. 9D). Further, antibodies purified from the same serum on absorbents from other antigen-positive clones reacted specifically with other polypeptides, not the $M_r >300,000$ polypeptide (data not shown).

It is concluded that FIRA is a very large polypeptide that is expressed in each isolate of P. falciparum tested, and that antibodies to the allele of FIRA expressed by FC27 cross-react with the alleles expressed by K1 and NF7.

Location and stage specificity of FIRA and its mRNA

The affinity-purified human antibodies and serum from mice immunized with clone Ag231 or members of the Ag231 family reacted with mature parasites (containing pigment) and also with cells containing immature (ring-form) parasites. The fluorescence over ring-infected cells was uneven and apparently distributed beyond the limits of the parasite. Hence it is likely that FIRA is external to the parasite, although no staining of the erythrocyte surface was detected when the antibodies were reacted in suspension with non-fixed parasitized cells or with lightly glutaraldehyde-fixed and air-dried monolayers of parasitized erythrocytes (12).

The stage specificity of FIRA is therefore in some ways analogous to RESA (2). Hybridization of cDNA prepared from mRNA of highly purified merozoites to the array of 133 colonies revealed another parallel with RESA. All members of the Ag231 family hybridized to merozoite cDNA. Remarkably, the only other clones in this array or in a separate array of 78 antigen positive clones, that hybridize to merozoite cDNA encode RESA (2,13). Hence FIRA and RESA mRNAs are unusual among mRNAs for *P. falciparum* antigens in that they are greatly enriched in merozoites.

FIRA Sequence

The chromosomal clone encompassing the AhaIII fragment, cloned in λgt10 and designated Ag231.5 has been fully sequenced. The gene contains an intervening sequence and is remarkably like RESA in overall structure. Exon 1 consists of a segment that may be a signal peptide (although it is very short), then a region of hydrophilic amino acid followed by a stretch of 32 uncharged amino acids. The intervening sequence is located immediately adjacent to this relatively hydrophobic segment. The remaining sequence is composed of blocks of repetitive and interspersed non-repetitive sequences. In all cases, the repetitive sequences occur as groups of 13 hexamers, but the most 5' group of these lack interspersed non-repetitive sequences - i.e. there is a block of 39 hexamers. It appears that a deletion at the 3' end has altered the linker - Aha join, so the structure at the 3' end is uncertain.

Cross-Reactions Amongst Repeats

Human antibodies affinity-purified on Ag231.6 (FIRA) when tested in an ELISA gave a very strong signal on Ag231.6, a weaker but very definite signal on Ag13.1.7.5 (RESA. 5' repeat), and no signal on Ag13 (RESA 3' repeat) (FIG. 10). This cross-reaction is consistent with the sequence homology between the repeats in these otherwise distinct antigens.

A full description of the preparation of recombinant DNA molecules, and of recombinant DNA cloning vehicles and vectors, of host cell-cloning vehicle combinations, and of the expression of polypeptides by host cells appears below.

REFERENCES

1. Kemp, D. J., Coppel, R. L., Cowman, A. F., Saint, R. B., Brown, G. V. & Anders, R. F. (1983) *Proc. Natl. Acad. Sci, USA* 80, 3787-3791.
2. Coppel, R.L., Cowman, A.F., Anders, R. F., Bianco, A. E., Saint, R. B., Lingelbach, K. R., Kemp, D. J. & Brown, G. V. (1984) *Nature* (London) 310, 789-792.
3. Ozaki, L. S., Svec, P., Nussenzweig, R. S., Nussenzweig, V. & Godson, G. N. (1983). *Cell* 34, 815-822.
4. Dame, J. B., Williams, J. L., McCutchan, T. F., Weber, J. L., Wirtz, R. A., Hockmeyer, W. T., Sanders, G. S., Reddy, E. P., Maloy, W. L., Haynes, J. D., Schneider, I., Roberts, D., Diggs, C. L. & Miller, L. H. (1984) *Science* 225, 593-599.
5. Coppel, R. L., Cowman, A. F., Lingelbach, K. R., Brown, G. V., Saint, R. B., Kemp, D. J. & Anders, R. F. (1983) *Nature* (London) 306, 751-756.
6. Stahl, H-D., Crewther, P. E., Anders, R. F., Brown, G. V., Coppel, R. L., Bianco, A. E., Mitchell, G. F. and Kemp, D. J. (1985). *Proc. Natl. Acad. Sci. USA.* 82, 543-547.
7. Stahl, H-D., Coppel, R. L., Brown, G. V., Saint, R. B., Lingelbach, K., Cowman, A. F., Anders, R. F. & Kemp, D. J. (1984) *Proc. Nat. Acad. Sci. USA* 81, 2456-2460.
8. Sanger, R., Nicklen, S. & Coulson, A. R. (1977) *Proc. Nat. Acad. Sci. USA* 74, 5463-5467.
9. Messing, J. & Vieira, J. (1982) *Gene* 19, 269-276.
10. Staden, R. (1980) *Nucl. Acids, Res.* 8, 3673-3694.
11. Atherton, E., Caviezel, M., Fox, H., Harkiss, D., Over, H., Sheppard, R. C. (1983) *J. Chem. Soc. Perkin Trans.* 1, 65-73.
12. Perlmann, H., Berzins, K., Wahlgren, M., Carlsson, J., Björkmann, A., Patarvoyo, M. E., and Perlmann, P. (1984) *J. Exp. Med.* 159, 1686-1704.
13. Anders, R. F., Coppel, R. L., Brown, G. V., Saint, R. B., Cowman, A. F., Lingelbach, K. R., Mitchell, G. F. and Kemp, D. J. 1984) *Molec. Biol. Med.* 2, 177-191.

We claim:

1. A recombinant DNA molecule encoding an antigen of *P. falciparum* selected from the group consisting of the Ring-Infected Erythrocyte Surface Antigen (RESA) and the Falciparum Interspersed Repeat Antigen (FIRA).
2. A recombinant DNA molecule according to claim 1 encoding all of the RESA antigen of *P. falciparum*.
3. A recombinant DNA molecule encoding all or an antigenic portion of the Falciparum Interpersed Repeat Antigen (FIRA) of *P. falciparum*.
4. A recombinant DNA molecule according to claim 1 encoding all of an antigen of *P. falciparum*, said antigen having the amino acid sequence shown in FIG. 1.
5. A recombinant DNA molecule according to claim 3 encoding all or an antigenic portion of an antigen of *P. falciparum* said antigen having the amino acid sequence shown in FIG. 7.
6. A recombinant DNA molecule according to claim 1 encoding an immunogenic polypeptide of *P. falciparum* selected from the group consisting of EENVEHDA, (EENV)$_4$ and DDEHVEEPTVAY.
7. A recombinant DNA molecule according to any one of claims 1-5, or 6, operatively linked to an expression control sequence.
8. A recombinant DNA vector comprising a recombinant DNA molecule having inserted therein a nucleotide sequence according to any one of claims 1-5 or 6 operatively linked to an expression control sequence, said vector being capable of expressing all or an antigenic portion of a protein encoded by said recombinant DNA molecule.
9. A recombinant DNA vector according to claim 8, wherein said nucleotide sequence and said expression control sequence are inserted into a bacteriophage.
10. A recombinant DNA vector according to claim 9, wherein said bacteriophage is bacteriophage λAmp3.
11. A host cell transformed with a vector comprising a recombinant DNA molecule operatively linked to an expression control sequence.
    said recombinant DNA molecule encoding one member selected from the group consisting of:
    (a) an antigen of *P. falciparum* selected from the group consisting of the Ring-Infected Erythrocyte Surface Antigen (RESA) and the Falciparum Interspersed Repeat Antigen (FIRA);
    (b) an antigenic portion of the amino acid sequence shown in FIG. 1;
    (c) an antigenic portion of the amino acid sequence shown in FIG. 7; and
    (d) an immunogenic polypeptide of *P. falciparum* selected from the group consisting of EENVEHDA, (EENV)$_4$ and DDEHVEEPTVAY.

* * * * *

UNITED STATES PATENT AND TRADEMARK OFFICE
CERTIFICATE OF CORRECTION

PATENT NO. : 5,126,264
DATED : June 30, 1992
INVENTOR(S) : David J. KEMP et al.

It is certified that error appears in the above-identified patent and that said Letters Patent is hereby corrected as shown below:

On title page, item [73],

Change Assignee from "The Walter and Eliza Hall Institute of Medical Research" to -- SARAMANE PTY., LTD. --

Signed and Sealed this

Twenty-third Day of April, 1996

Attest:

BRUCE LEHMAN

*Attesting Officer*     *Commissioner of Patents and Trademarks*